United States Patent [19]
Avila et al.

[11] Patent Number: 4,989,372
[45] Date of Patent: Feb. 5, 1991

[54] PRECISION RADIAL ARM SAW FOR COMPOSITE MATERIALS

[75] Inventors: Steven J. Avila, Federal Way; Charles R. Reid, Seattle, both of Wash.

[73] Assignee: The Boeing Company, Seattle, Wash.

[21] Appl. No.: 225,333

[22] Filed: Jul. 27, 1988

[51] Int. Cl.$^5$ .............................................. B24B 7/22
[52] U.S. Cl. ................... 51/34 C; 51/217 R; 51/37; 125/13.01
[58] Field of Search ............... 51/34 C, 34 R, 34 D, 51/37, 217 R, 216 R; 125/13, 14, 13.01

[56] References Cited

U.S. PATENT DOCUMENTS

| | | | |
|---|---|---|---|
| 2,685,766 | 8/1954 | McGovern | 51/37 |
| 2,774,191 | 12/1956 | Bouchez | 51/34 C |
| 3,878,654 | 4/1975 | Wendt, III et al. | 51/34 D |
| 4,188,754 | 2/1980 | Yamamoto | 51/37 |

FOREIGN PATENT DOCUMENTS 0052257 3/1985 Japan .................................. 51/34 D

*Primary Examiner*—Robert A. Rose
*Attorney, Agent, or Firm*—Seed and Berry

[57] ABSTRACT

A precision radial arm saw includes a diamond saw blade for wet cutting a material. The radial arm saw is slidably coupled two shafts which extend in a horizontal plane above the cutting surface. The shafts are attached to a frame which is rotatably supported in a central rigid by a support beam. A lever arm is adjustable coupled to the support beam to ensure that the shafts remain horizontal as the radial arm saw is slid along them. The shafts are positioned sufficiently far apart that the saw is held in a stable position, without wobbling or tilting while cutting the material. The size of the material cut is precisely determined by using a spacer plate adjacent a precision set fence. Spacer bars may be placed between the spacer plate and the fence to provide precise cutting of specimens of different sizes.

8 Claims, 6 Drawing Sheets

PRECISION RADIAL ARM SAW FOR COMPOSITE MATERIALS

TECHNICAL FIELD

This invention relates to preparation of specimens for destructive testing, and more particularly, to a precision radial arm saw for preparing the specimens to be tested.

BACKGROUND ART

Aircraft structures are increasingly being constructed from new materials. It is desirable, and often required, that significant testing be performed on the new materials prior to their being incorporated into an aircraft structure. Once the material has been determined suitable for use in an aircraft, each lot of material must be tested at various stages of the production to ensure that the material is properly constructed. The testing includes the testing of incoming material from a third party prior to constructing the material for use in the aircraft. The testing may also include testing the material after final construction, just prior to incorporation into an aircraft structure. This invention is related to U.S. patent application Ser. No. 173,485, filed Mar. 25, 1988 by Reid et al. which describes other methods and apparatuses for preparing specimens.

One of the types of material recently in use in an aircraft structure is a composite material. Composite materials include various resins, fibers and graphite epoxy composites of various compositions. One method of testing the graphite epoxy composite material is load test samples of the material. To load test samples, test specimens are produced from the sheets of material which will be used in the aircraft structure. The specimens are subjected to destructive load tests to determine the loads which the material will carry prior to failure. The destructive load tests include tensile tests, in which the specimen is placed in tension and the load increased until the member fails, and a compression test, in which the test specimen is placed in compression and the load increased until the specimen fails. Ideally, the amount of load held by the specimen until failure is an indication of the quality of the material. If all of the specimens from a lot fail under a very small load, the lot of material is likely defective. If the lot of material is found defective, it will be rejected for use on the aircraft.

One problem in the prior art is the difficulty of producing specimens which accurately reflect the quality of the lot of material. In the prior art, the specimens are prepared from the larger sheet taken from the lot. The specimens are cut from the sheet and tested in the laboratory. Frequently, using prior art techniques of specimen testing, the load carried by the specimens within the single sheet were significantly different. Some specimens fail under very small loads, while other specimens from the very same sheet carry large loads prior to failure. When the failure point of specimens within the same lot is not uniform, the quality of the lot is difficult to determine and often requires additional specimens, with further testing to be performed. A further problem in the prior art is that significant time is required to prepare the specimens using prior art techniques. Additional time is required to prepare the large number of specimens for testing until a sufficiently uniform test result is achieved to provide an indication of the quality of the material being tested.

SUMMARY OF THE INVENTION

It is therefore an object of this invention to provide a method of preparing specimens for testing which ensures that the specimens are representative of the characteristics of the material from which the specimens were prepared.

It is an object of this invention to provide a method of cutting specimens from a sheet of material which will produce specimens that are uniform with respect to each other.

It is another object of this invention to provide an apparatus for cutting specimens in a precise and uniform manner.

It is another object of this invention to provide a radial arm saw which leaves a smooth surface on a specimen along the edge which was cut.

These and other objects of the invention are accomplished by providing a precision radial arm saw for wet-cutting the composite material. The radial arm saw assembly is supported by two shafts. The radial arm saw is coupled to the shafts with recirculating roller bearings to ensure smooth and uniform motion of the radial arm saw assembly. The shaft supports for the radial arm saw are positioned sufficiently far apart that the saw is stably mounted and does not wobble or tilt. Preferably, the distance between the two support shafts of the radial arm saw is such that the angle formed by planes extending from the cutting tip of the saw blade to the center of each of the support shafts is approximately 30 degrees.

The shafts are supported at each end by a frame which is supported in the center by an overhead support beam. The support beam is rigidly coupled to a table. A rigid stiffening beam extends underneath the table for a length substantially equal to the length of the shafts. The stiffening beam is rigidly coupled to the table at a plurality of positions. An adjustment bolt is coupled from the support beam to the stiffening beam to ensure that the support beam remains level for any position of the saw along the shafts.

A precision set fence is solidly attached to the table at a precise location. A spacer plate, having a clamp thereon, is movably attached to the table. The spacer plate is mounted with slots therein to permit the spacer to be moved to different positions with respect to the set fence and tightened. Precision spacer bars may be placed between the fence and the spacer plate to provide additional precision cut sizes. The radial arm saw cuts the part with a nonclimbing cut, contrary to the operation of conventional radial arm saws. A clamp is provided for holding the part in position while the cut is being made by the saw.

DETAILED DESCRIPTION OF THE INVENTION

Destructive testing of samples of a material is often required to determine the quality of a material to be used in a particular structure, such as an aircraft. When testing a material using a destructive test, generally a sample of the material is removed from the lot, a specimen is prepared and the specimen is load tested to failure. Numerous specimens are generally prepared from the sample sheet. Each of the specimens is subjected to the same destructive test. If all of the specimens fail under approximately the same load, the test results are generally considered valid. If the load under which all the specimens fail is low, the material is generally defective and, if defective, is not suitable for use in the aircraft. If all the specimens carry a large load prior to failure, the lot is certified as passing that particular inspection. However, if some of the specimens fail under a very light load and other specimens fail under a very heavy load, the test results are inconclusive and the quality of the material is not known. A different sample may then be taken from the lot, and specimens prepared from that sample and tested to determine the quality of the lot of material. The testing of specimens continues until the testing is sufficiently conclusive of the quality of the lot of the material.

Figure 1:
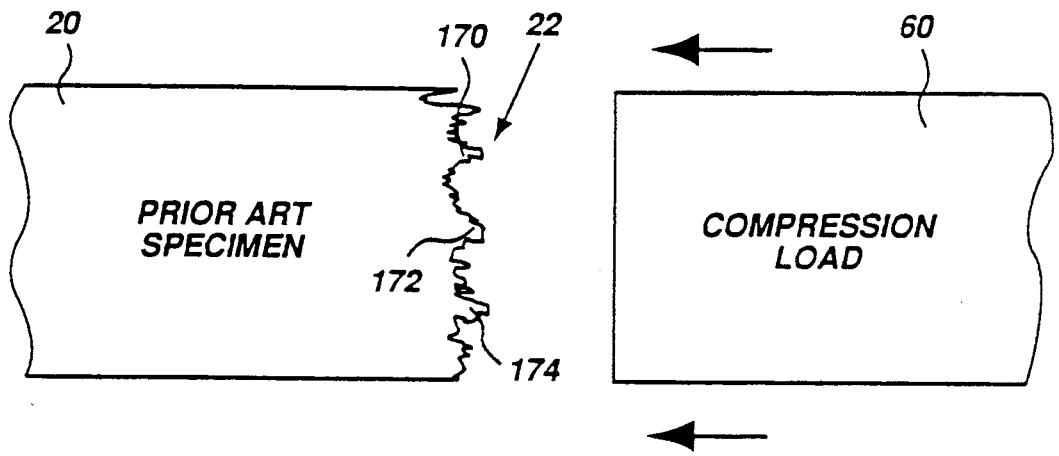
FIG. 1 is a side elevation of a compression test specimen prepared according to the methods and apparatus of the prior art.

A specimen 20 prepared according to methods of the prior art is illustrated in FIG. 1. The specimen shown is a graphite epoxy composite material, though specimens of other materials may be used and fall within the scope of this invention. The specimen 20 includes a surface 22 to which the compression load is applied for determining the load which can be carried by the specimen prior to crushing. The surface 22 of the prior art specimen contains irregularities 70, 72 and 74 created during the preparation of the specimen. The irregularities are magnified in FIG. 1 to illustrate the problems of the prior art. As the compression load is applied to the surface 22, the anvil 60 contacts the peaks of the irregularities, such as 70, 72 and 74, prior to contacting the other portions of the surface. The peaks of the surface 22 support the entire load from the compression anvil 60, while the other regions of the surface 22 do not support the load. Many materials, for example, a composite material, such as a graphite-epoxy, other composite material or the like do not evenly distribute an external load to different internal portion of the specimen. The specimen carries the entire load on peaks 70, 72 and 74. When these peaks fail, the entire specimen fails and is destroyed. Thus, the specimen prepared by the prior art techniques, as shown in FIG. 1, may be destroyed after holding only ten percent of the expected load, even though the specimen may have been made from quality material. The specimen failed at a low load because the surface 22 was not sufficiently smooth. Other specimens from the same lot may fail at significantly different loads, depending upon the smoothness of surface 22, the number of peaks and valleys and other irregularities in the surface 22 to which the compression load is applied. The results of the test are therefore not uniform and are not an accurate indication of the quality of the material from which the specimen was produced.

The surface roughness of specimens made according to the prior art is generally in the range of 230 to 150 RMS, an industry standard of surface roughness. A surface roughness in excess of 150 RMS is generally so rough that uniform and reliable test results are not obtainable. Even with a roughness of 32 RMS, the results are not as uniform as desired to accurately reflect the quality of the material being tested.

A further requirement of the specimen is that it be an exact size and shape, within strict tolerances, to ensure that the test results are uniform and accurate. If one specimen is slightly thinner or thicker than other specimens, the test results will be different than for other specimens and additional testing may be required.

Figure 2:
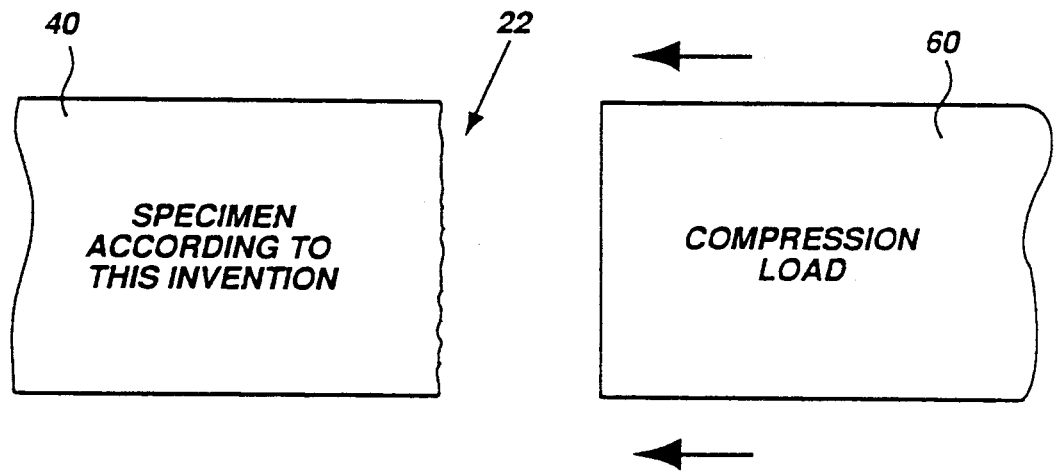
FIG. 2 is a side elevation of a compression test specimen produced according to the invention.

A specimen 40 made according to this invention is illustrated in FIG. 2. The surface 22 of the specimen to be tested is extremely smooth and uniform. When a compression load is applied, the load is carried by a majority of the fibers in the specimen, preferably over ninety percent of the fibers. The load at which the specimen fails is therefore an accurate reflection of the quality of the material.

The specimen 40 produced according to this invention preferably has a surface smoothness less than 15 RMS. Further, the size and shape of each test specimen is exactly the same as other test specimens, within tight tolerances.

Figure 3:
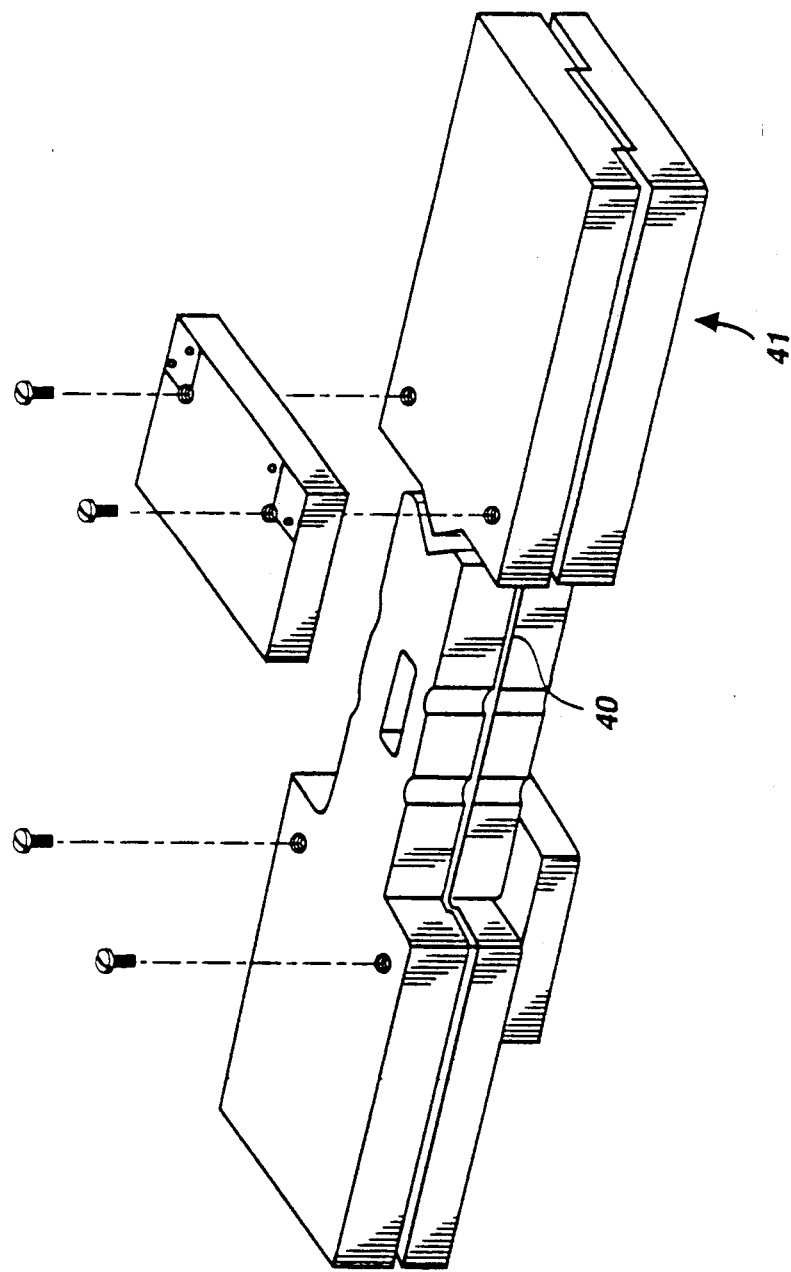
FIG. 3 is an isometric view of an open hole compression test specimen produced according to this invention.

An open-hole compression test specimen 40 and fixture 41 are illustrated in FIG. 3. The specimen 40 is placed in the open-hole compression fixture 41 for destructive testing. An industry standard open-hole compression fixture may be used, as is well known in the industry. A compression load is placed on specimen 40 until failure, as is known in the art. The specimen 40 must be of an exact size and shape, within tight tolerances, to accurately reflect the quality of the material being tested. The ends and edges of the specimen must also be smooth, preferably smoother than 15 RMS to permit the destructive test to be uniform between specimens and to accurately reflect the quality of the material. Specimens other than the anvil compression specimen and open-hole compression specimen may also be produced according to this invention. The specimens must also have smooth surfaces to provide uniform test results. For example, tension specimens must be sufficiently smooth on all edges to provide uniform test results.

Producing specimens having a smooth face 22 is accomplished according to this invention using a wet-cutting diamond blade saw. Previous to this invention, the use of a wet-cut saw blade for cutting graphite-epoxy composite material was not considered possible.

A radial arm saw assembly 39 and support assembly 37 for preparing specimens according to this invention is illustrated in FIGS. 4–8. The radial arm saw assembly 39 diamond saw includes a blade 48 coupled to a shaft 50 of an air motor 52 having an air supply 43. The blade includes a diamond cutting surface 105 on the edge and sides of the blade, as is known in the art of diamond cutting saw blades. A locking nut 54 firmly holds the blade 48 onto the shaft 50. Washers 56 and 58 are circular washers coupled to the motor shaft 50 on either side of blade 48. The washers extend from the shaft 50, in contact with the blade 48, along either side of the blade. The washers extend over a majority of the surface of the blade. The washers ensure that the saw blade 48 is rigidly held in a single plane of rotation about shaft 50 as the blade rotates. The washers minimize the wobble of the saw blade by applying a rigid holding force extending from the shaft 50 outward towards the edge of the blade 48. The washers may extend to the edge of the blade minus the thickness of the part to be cut to provide maximum stability in the rotation. A water hose 47 having a nozzle (not shown) adjacent the cutting edge of the blade 48 provides a stream of water on the blade during a cutting operation to provide a wet-cut. A blade guard 60 extends substantially around the blade 48 to aid in containing the water sprayed on the blade during the cutting operation. The guard further provides a rigid, stable connection between the end of the motor 52 and the saw mount 60, the guard extending completely around the blade 48 as a rigid unit. The saw blade assembly includes a handle 57 which the user grips and pushes away from him in cutting the material.

A sheet of material 42 from which the specimen is to be cut, is shown just prior to being cut in FIGS. 4–8. The cut is performed as a nonclimbing cut, that is, the saw blade is moving upward at the upper surface of the material 42. The saw blade rotates clockwise as it is pushed away from the user and into the material, as shown by arrows 59 and 61 of FIG. 5. Conventional radial arm saws cut with a climbing cut, that is, the saw blade is moving downward at the upper surface of the material. Further, a conventional radial arm saw is pulled by the user from the rear, towards the user, through the material to be cut. When the conventional radial arm saw blade is cutting with a climbing cut the saw blade "climbs" the material being cut, that is, the saw blade pulls itself into the material as it cuts the material. In conventional radial arm saws this is desired and produces a much easier cut. However, a conventional radial arm saw cut of composite material causes the saw to "rush" the cut and move into the material faster than desired. If the saw blade is moved too quickly in the cutting action the cut surface 22 is not as smooth as required. Use of a nonclimbing cut permits the saw blade 48 to be moved slower, at its own cutting pace during the cut, to ensure that a smooth cut surface 22 is obtained.

Motor 52 is an air motor. Previously, air motors have not been used as the motors for radial saws. The disadvantage of the use of air motors for a radial arm saw is that if an air motor slows down slightly, the air motor may stop completely rather than operating at a slightly slower RPM. The disadvantage of the use of an air motor for a radial arm saw has been overcome in this invention. The radial arm saw of this invention is a wet-cut saw using water as a lubrication for a diamond saw blade. This aids the saw blade to have a constant speed during the entire cutting operation. The water, which is being used as a lubricant during the cut, may spray onto motor 52. If motor 52 is an electric motor, special insulation, shielding and isolation are required to ensure that the water does not enter the electrical wiring and short out an electric motor. By using an air motor, the insulation problems of wet cutting with an electric motor are avoided. An additional feature of the radial arm saw, in combination with an air motor, is that the direction of the cut is a nonclimbing cut of the radial arm saw as has been described. Because a nonclimbing cut is being done by the air motor, the saw cut is done more slowly, which decreases the likelihood that the saw will be slowed down during the cutting operation.

The support assembly 37 includes support shafts 70 and 72 coupled to a frame 74 at each end. The saw blade assembly is coupled to the support assembly by saw mounting member 60 and ball bearings. Saw mounting member 60 has two pairs of ball bearings thereon, a front pair 62 and 64 and a rear pair 66 and 68. The ball bearings are recirculating ball bearings which provide smooth and precision rolling along shafts 70 and 72.

Figure 4:
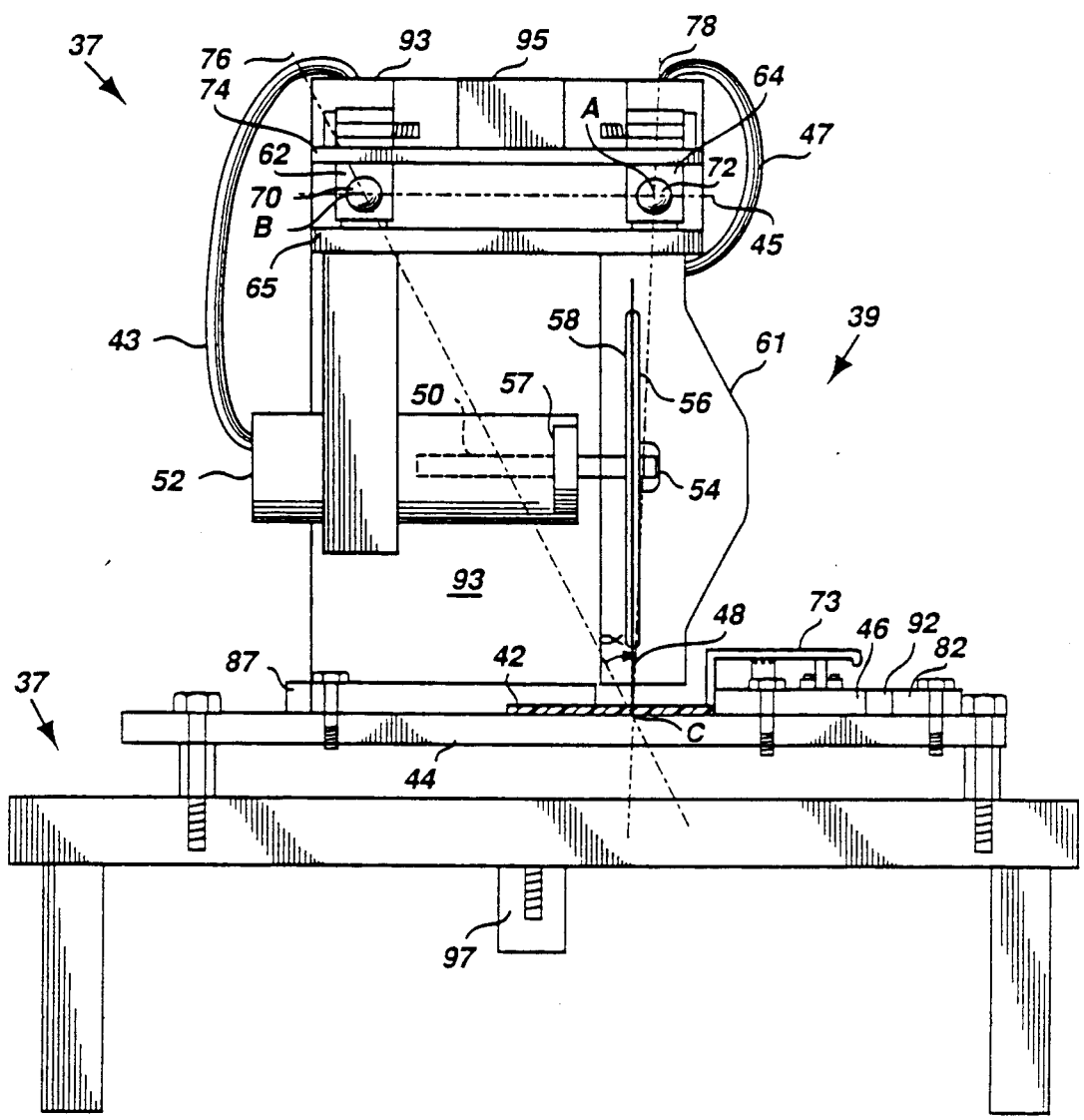
FIG. 4 is a front elevation of the precision radial arm saw and support assemblies of this invention.
Figure 5:
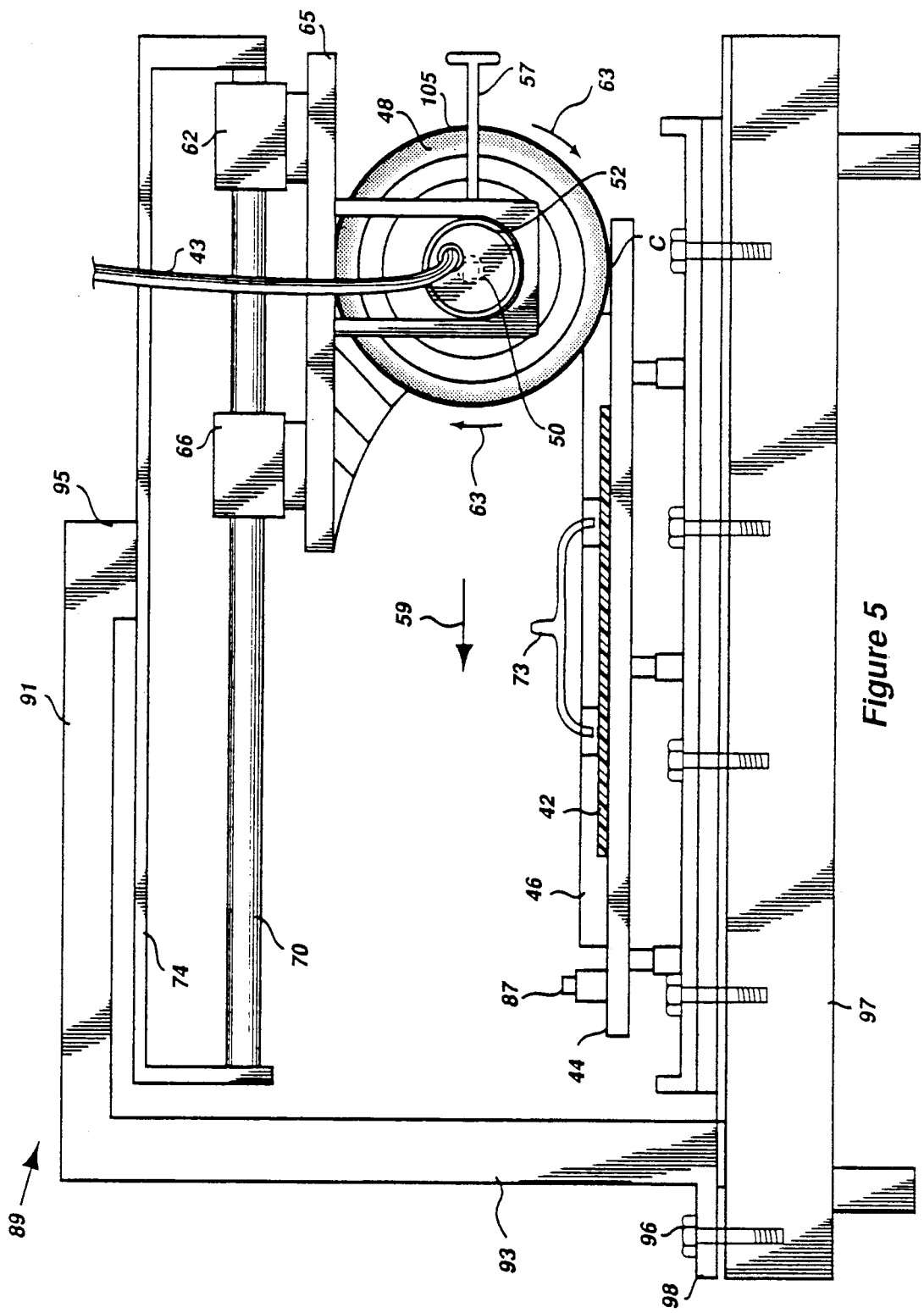
FIG. 5 is a side elevational view of FIG. 3.
Figure 6:
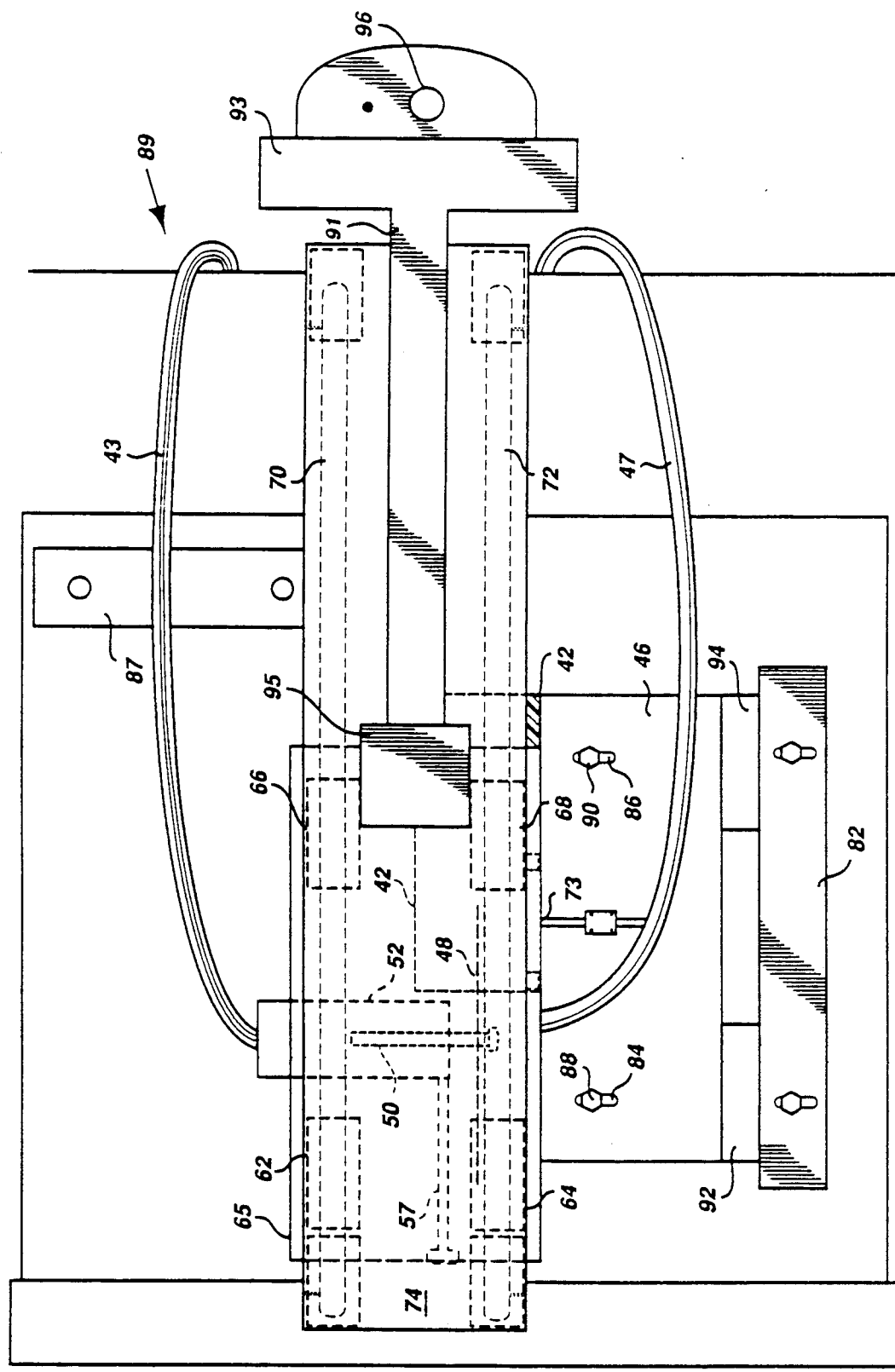
FIG. 6 is a top plan view of FIG. 3.

The shafts 70 and 72 are spaced sufficiently far apart to provide a stable support for the radial saw assembly. The required distance between the two shafts is determined based on the position of the tip of the saw blade intersecting each of the shafts. For example, the cutting tip surface of saw blade 48 is located at point C, as shown in FIG. 4. A plane 76 extends from point C to the center of shaft 70, point B. Another plane 78 extends from point C through the center of shaft 72, point A. The angle $\alpha$ is formed between the two planes 76 and 78, as shown in FIG. 4. Preferably, the angle $\alpha$ is approximately equal to or greater than thirty degrees. If the angle $\alpha$ is significantly less than thirty degrees, the bearing shafts 70 and 72 will be so close together as to not provide necessary support for the radial arm saw assembly 39 to ensure that the saw does not wobble or tilt during a cutting operation. The angle $\alpha$ can be greater than thirty degrees if desired; for example, forty-five degrees or the like. However, as the angle becomes greater, the distance between shafts 70 and 72 increases significantly, causing the radial arm saw to take up more room. While having the angle $\alpha$ greater provides more stability, an angle of approximately thirty degrees is preferred to provide sufficient stability at a minimum space usage.

The radial arm saw includes a cutting table 44 on which the part 42 is held during the cut. A precision-set fence 82 is rigidly attached to the cutting table 44 at a desired location. The precision-set fence is set at an exact position with respect to the saw blade 48. It may take over a day using sophisticated precision equipment, to set fence 82 in an exact position with respect to the saw blade 48. In the prior art, the fence 82 was repeatedly moved and realigned each time a different sized part was cut. However, according to this invention, a plurality of different spacers are provided between the precision saw fence and the part 42, the size and placing of the spacers depending upon the size of the sample to be cut. The spacers include a spacer plate 46 to which a clamp 73 is attached. The clamp 73 is provided to firmly and rigidly hold the part 42 to the table 44. The spacer plate includes slots 84 and 86 through which bolts 88 and 90 respectively extend for rigidly coupling the spacer plate 46 to the cutting table 44 at a plurality of locations. A second set of spacers, spacer bars 92 and 94 may be positioned between the precision-set fence and the spacer plate to permit precision spacing of the part with respect to the saw blade at different positions.

The precision-set fence is positioned the distance from the saw blade corresponding to the largest part to be cut. When the largest part is to be cut, each of the spacers is removed and the part is firmly placed against the precision-set fence. The sheet 42 is then cut. Generally, the cut of the material against fence 82 is a rough cut to prepare the sheet 42 for further cutting to provide precision-cut specimens. A clamp for the rough cut is not required, but could be used if desired. When a piece of a shorter width is desired to be cut, spacer plate 46 is coupled between the precision-set fence and the saw blade. The precision spacer plate has a clamp 73 thereon to firmly hold the part 42 in firm contact with the table 44. The clamp 73 is required because the nonclimbing cut of the radial arm saw tends to lift the material 42 from the table. If there is sufficient room, the user may hold the material 42 down with his fingers. However, a mechanical clamp is preferred to ensure that the part is held firmly in a flat, horizontal plane while the cut is being made. The exact width of spacer plate 46 will depend upon the dimensions of the largest speciment to be cut. The spacer plate 46 may be a relatively wide spacer, such as that illustrated in FIGS. 3 and 5, or a more narrower spacer. The spacer 46 includes slots 84 and 86, which permit the spacer to be adjustably mounted from a position in firm contact with the precision-set fence 82 to a position closely adjacent the saw blade 48. When the spacer 46 is firmly abutting the set fence, the widest specimen may be cut. When a slightly thinner specimen is desired to be cut, the bolts 88 and 90 are loosened and the spacer 46 is slid towards the saw blade 48. Spacer bars 92 and 94 are placed between the spacer plate 46 and the precision-set fence. The spacer bars 92 and 94, while shown as two separate spacers, could be a single long spacer bar extending between the set fence and the first spacer 46, if desired. The second set of spacers 92 and 94 are precision cut to provide an exact distance between spacer plate 46 and the saw blade 48. The spacer 46 is slid firmly against the spacers 92 and 94 to provide a known and uniform width for specimen 20. In the event a slightly more narrow specimen is to be cut, the spacer bars 92 and 94 are removed and a thicker spacer bar is placed between the fence 82 and spacer plate 46 which moves the spacer 46 closer to the saw blade 48. A plurality of different width spacer bars may be placed between the spacer plate 46, having the clamp thereon, and the precision-set fence 82, as desired. The advantage of using a spacer plate and a spacer bar, is that the spacer plate 46 always abuts the specimen in the final cut. The edge of the plate 46 is formed to be in contact with the material 42. The plate 46 may have a clamp 73 positioned thereon which may be repeatedly used on specimens of many different sizes. Rather than replacing the spacer plate 46 with a different spacer having the required exact dimensions, the spacer bars placed between the spacer plate 46 and the precision fence determine the additional width of the specimen to be cut. The use of a fixed spacer plate and a plurality of spacer bars saves on cost and materials in preparing precision spacers.

An adjustment bar 94 comprised of a large, rigid metal member extends from the rear of support table 104 forward for a distance approximately equal to the length of shafts 70 and 72. A precision height-adjusting bolt 96 extends through a flange 98 of the support portion 93 and into the adjustment bar 94. Tightening or loosening the bolt 96 provides precision tension on overarm support portion 91. One advantage of the invention is that the saw blade 48 moves precisely horizontal with respect to the material 42 to be cut. One disadvantage of the prior art radial arm saw support assemblies is that the saw did not move precisely in a horizontal plane along the entire travel length of shafts 70 and 72. When the saw assembly 39 was at either end of the shafts, such as shown in FIG. 4, the weight of the saw assembly 39 at the far end of the shafts caused the entire saw assembly, including the cutting blade 48, to sag slightly. The shafts 70 and 72 act as lever arms to multiply the effect of the weight of the saw assembly 39 at the ends of the shaft on joint 95. The downward movement of blade 48 due to sagging at each end of its travel is very slight, however, in the prior art there is a measurable difference between the height of blade 48 at the far end of the shaft and the height of the blade 48 at the center of the shafts, just below joint 95. Even though overarm support member 89 is made of cast iron or high-quality steel, the weight of the saw, through lever arms 70 and 72 is sufficient to cause some sagging. The difference in height as a cut is made may be sufficient to create an undesired roughness in the surface 22 being cut.

In producing specimens according to this invention, it is desired that the cutting edge of the blade tip 48 move generally uniform and horizontal relative to the member 42 being cut for the entire length of the cut. Bar member 94 acts as a lever arm, counteracting the weight of radial arm saw assembly 39 at the extended ends of shafts 70 and 72. The support for the radial arm saw 93 is coupled through the lever arm 94 through bolt 96 to permit precise the minute adjustments in the horizontal plane of travel of the tip of the blade 48. The diamond cutting surface 105 is held in an exact horizontal relationship to the material to be cut. Holding the blade in the same horizontal plane is important for a diamond blade producing a smooth surface 22 because the diamond edge extends partially along the sides as shown by 105. A smooth cut is provided if the surface being cut always contacts the diamond part of the saw and the saw moves generally horizontal. While the adjustment lever arm 94 is shown extending the entire length of the table, substantially the length of the shafts 70 and 72, the adjusting lever arm 94 need not necessarily be this long to provide the required additional support. If sufficient lever arm multiplication is provided to hold the radial arm saw support shafts 70 and 72 precisely level through the entire travel of the radial saw assembly 39, then the material 42 will be smoothly cut.

The sagging of the saw assembly at either end of the shafts could be compensated for by tilting material support surface 44 slightly at each end, the amount of tilt corresponding to the sag of the saw. Other techniques to ensure an exactly horizontal travel of the saw during the cut relative to the material 42 could also be used. For example, the frame 74 could be rigidly coupled at each end to a large frame, the frame 74 not being rotatable. The technique of using a lever arm below the table to counteract the effect of the shafts acting as a lever arm is efficient and economical. The use of adjustment bolt 96 through steel flange 98 permits precise changes in the horizontal travel of the saw assembly to be made as needed.

An air supply line 43 provides air to the motor 52 to provide the power to turn the shaft 50. A water line 47 provides water to a nozzle (not shown) which sprays a stream of water onto the blade 48 continuously during its operation. A drain table 104 collects the water falling from the cutting surface and recirculates it for repeated use in the water line lubrication system.

Figure 7:
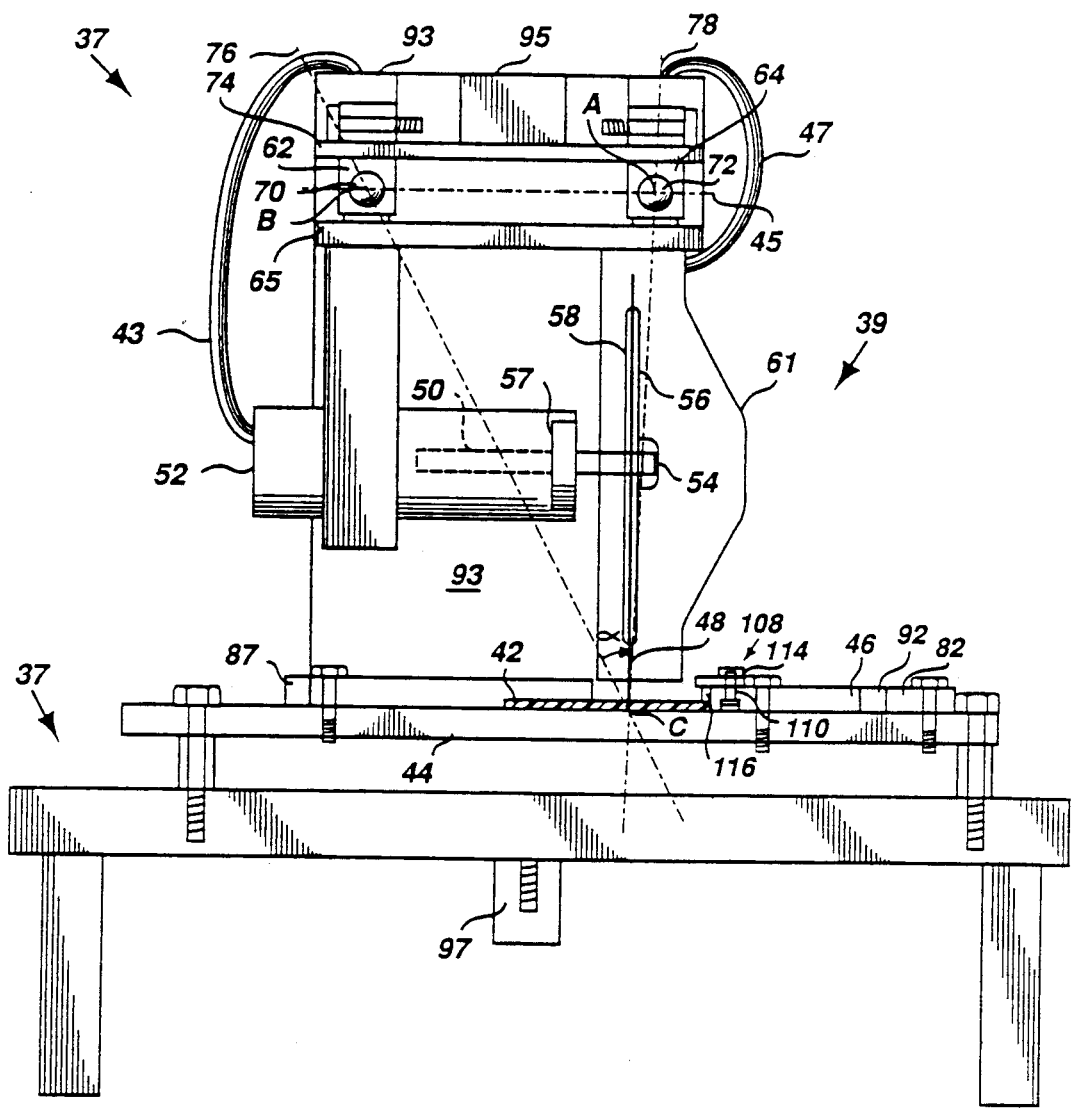
FIG. 7 is a front elevation of an alternative embodiment of the precision radial saw and support assemblies.

Clamp 96 may be replaced with a pneumatic clamp 108, as shown in FIG. 7. The pneumatic clamp 108 includes a piston 110 in a cylinder 112. An enlarged head 114 at the upper end of piston 110 engages a clamping member 116. When the pneumatic piston is retracted the clamping member 116 is pulled downward by enlarged head 114, onto the part 42, firmly holding it in position. Any other clamping device to firmly hold part 42 in position during the cut may be used if desired.

The method of preparing specimens according to the invention is as follows. The part 42 is first laid on the cutting table against the 90° set fence 87 for a trim cut. The material 42 is then placed adjacent the 0° set fence without a spacer for a length cut, generally, 12 inches. Then the material 42 is rotated 90° and set against the 90° fence for a squaring trim cut. Then the spacer plate 46 which was machined to an exact size to accommodate a specific size specimen, is placed against the set 0° fence and bolted in place. The spacer plate 46 has a clamp 96 mounted on it to hold down the specimen while the cut is made. Now every cut is to the exact size as determined by the spacer plate. To change the size of the specimen, spacer bars are placed between the spacer plate 46 and the set fence 82. This achieves controlled widths at a production rate without the time-consuming and complex operation previously required.

We claim:

1. A radial arm saw comprising:
   a cutting surface for retaining a specimen thereon while cutting said specimen;
   a clamp for firmly holding said specimen to said cutting surface;
   a plurality of support shafts positioned above said cutting surface;
   a support beam coupled to said support shafts, said support beam having a horizontal portion and a vertical portion;
   a radial arm saw slidably coupled to said support shafts;
   a rigid lever arm coupled to said support beam for retaining said support beam in a generally horizontal plane with respect to said cutting surface as said saw is slid along said support shafts.

2. The saw according to claim 1 wherein said lever arm is adjustably coupled to said vertical portion.

3. The saw according to claim 2 wherein said lever arm extends underneath said cutting surface.

4. The saw according to claim 1 wherein said support shafts are rotatably mounted to said support beam.

5. A radial arm saw comprising:
   a cutting surface for retaining a material thereon for cutting;
   a saw blade coupled to a radial arm saw positioned adjacent said cutting surface;
   a fence rigidly coupled to said cutting surface a predetermined distance from said saw blade;
   a clamp for rigidly holding a material to be cut to said cutting surface;
   a spacer plate having slots therein for rigidly coupling said spacer plate to said cutting surface at a plurality of different positions; and
   a spacer bar positioned between said spacer plate and said fence for positioning said spacer plate a predetermined distance from said saw blade.

6. The radial arm saw according to claim 5 wherein said radial arm saw blade cuts said material with a non-climbing cut.

7. The radial arm saw according to claim 5 wherein said spacer plate includes said clamp thereon.

8. The radial arm saw according to claim 5 wherein said clamp includes a pneumatic clamp coupled to said cutting surface.

* * * * *